(12) United States Patent
Huang et al.

(10) Patent No.: US 9,301,983 B2
(45) Date of Patent: Apr. 5, 2016

(54) **COMPOSITION AND METHOD OF *LACTOBACILLUS REUTERI* GMNL-89 IN TREATING TYPE 2 DIABETES**

(71) Applicant: GenMont Biotech Inc., Tainan (TW)

(72) Inventors: Hui-Yu Huang, Taipei (TW); Yi-Hsing Chen, Tainan (TW); Feng-Ching Hsieh, Pingtung County (TW)

(73) Assignee: GenMont Biotech Inc., Tainan County (TW)

( * ) Notice: Subject to any disclaimer, the term of this patent is extended or adjusted under 35 U.S.C. 154(b) by 0 days.

(21) Appl. No.: 14/200,162

(22) Filed: Mar. 7, 2014

(65) Prior Publication Data

US 2015/0250835 A1   Sep. 10, 2015

(51) Int. Cl.
| | |
|---|---|
| *A61K 49/00* | (2006.01) |
| *A01N 63/00* | (2006.01) |
| *C12N 1/20* | (2006.01) |
| *A61K 35/747* | (2015.01) |
| *A61K 45/06* | (2006.01) |
| *A23L 1/30* | (2006.01) |
| *A61K 9/00* | (2006.01) |

(52) U.S. Cl.
CPC .............. *A61K 35/747* (2013.01); *A23L 1/3014* (2013.01); *A61K 9/00* (2013.01); *A61K 45/06* (2013.01); *A23V 2002/00* (2013.01); *A23Y 2220/71* (2013.01)

(58) Field of Classification Search
CPC ..... A61K 35/66; A61K 35/74; A61K 35/744; A61K 39/00; A61K 39/09
USPC ............................. 424/9.2, 93.45; 435/252.9
See application file for complete search history.

(56) References Cited

U.S. PATENT DOCUMENTS

| | | | |
|---|---|---|---|
| 7,901,926 B2 | 3/2011 | Yu et al. | |
| 8,298,526 B2 | 10/2012 | Leu et al. | |
| 2011/0300117 A1* | 12/2011 | Leu et al. | ................... 424/93.44 |

* cited by examiner

*Primary Examiner* — Rodney P Swartz
(74) *Attorney, Agent, or Firm* — WPAT, P.C.; Anthony King (57) ABSTRACT

Present invention features a novel use of *Lactobacillus* for treating type 2 diabetes, wherein the *Lactobacillus* is *Lactobacillus reuteri* GMNL-89 with the deposition numbers of BCRC 910340 and CCTCC M 207154 and comprises of live, dead bacteria or supernatant of the bacterial culture(s) and a pharmaceutically acceptable vehicle. The invention also discloses the efficacies of the indicated *Lactobacillus* strain including anti-oxidative enzyme activity, anti-inflammation, reduction of blood glucose level, reduction of triglycerides, reduction of total cholesterol, reduction of LDL, increase of HDL and improve insulin utilization.

10 Claims, 4 Drawing Sheets

COMPOSITION AND METHOD OF *LACTOBACILLUS REUTERI* GMNL-89 IN TREATING TYPE 2 DIABETES

BACKGROUND OF THE INVENTION

1. Field of the Invention

The present invention relates to new use of *Lactobacillus* isolates, in particular, to the technical field of treatments for type II diabetes.

2. Description of the Prior Art

Diabetes Mellitus is a metabolism disease of many pathogens. It is a disease caused by extensive metabolism dysfunction induced by the defects produced in the secretion or action of insulin. The main feature of diabetes consists of constant chronic high blood sugar, as well as metabolic disorder of protein, lipid, water, electrolyte and the like.

Clinically, diabetes is classified mainly into two types:

Type 1: Insulin-dependent diabetic mellitus (IDDM), occurs mostly before the age of 30 as such been named as "Juvenile-Onset diabetes", but actually it may occur at any age. Type 1 diabetes is an autoimmune disease in which the immune system itself attacks β cells in the islets of Langerhans in the pancreas. Its cause is involved with personal genetics, virus infection, or damage of toxic substance on β cells of the pancreas, antibodies against β cells produced by autoimmunology, and attacking on β cells by cellular immune action. Eventually, the pancreas of the subject cannot secrete insulin normally and becomes extremely susceptible to toketoacidosis and in need of treatment of insulin injection.

Type 2: Non-insulin dependent diabetic mellitus (NIDDM), occurs mostly after the age of 40 years. Most patients with NIDDM are overweight and therefore this type has been called "maturity-onset diabetes" in the past. However, it may occur in young men and familial occurrence is often found. This type of diabetes consists of more than 95% of total diabetes population in Taiwan. This type of diabetes is caused by defects in insulin secretion, and insulin resistance; in which, though decrease of insulin secretion in some patients may be observed, most patients have acceptable ability to produce insulin. Therefore, its treatment depends largely on dietary control and oral administration of blood glucose-lowering drugs to control blood glucose level and does not need insulin injection immediately. In addition, most patients may be accompanied by insulin resistance. Formation of insulin resistance comes primarily from the excess secretion of insulin (hyperinsulinemia) by the β cells in the islets of Langerhans in the pancreas, which causes decreased insulin sensitivity of peripheral tissues such as skeleton muscles, adipose tissues, liver and the like, thereby diminishes the utilization of glucose in these tissues, and hence induces the phenomenon of high blood sugar. Progression of this type is slow, no typical diabetes symptom emerges at the early stage and hence it is not easy to detect. It is accompanied usually by chronic complications such as diabetic pathogenic change of large vessels (for example, cardiomuscular infarction and brain stroke), small vessels (for example in kidney, retina and nerve) and the like.

In addition, subjects of type 2 diabetes are accompanied usually with abnormal lipid metabolic conditions, such as increasing of triglyceride (TG) concentration, lowering of high density lipoprotein cholesterol (HDL-C) concentration and increasing of low density lipoprotein cholesterol (LDL-C) concentration in the plasma. This syndrome may incur in type 2 diabetes subjects with risk of cardiovascular diseases. Further, it has been pointed out that serious diabetes subjects might diminish their ability to clear blood lipid in the liver. When triglyceride and low density lipoprotein cholesterol has been accumulated continuously to some extent, pathological change of liver cells may occur to form non-alcoholic fatty liver and affect the liver function severely.

Other than the administration of insulin, two additional ways for treating diabetes consists of non-drug and drug treatments. Non-drug treatment resides mainly on dietary regulation and sport. Whereas in the aspect of drug treatment, its primary object involves rising the deficiency of insulin, regulating down the high blood sugar after meal, improving insulin resistance and the like. At present, drugs used to treat diabetes may include:

(1) Sulfonylurea: The main mechanism of this type of drug is to promote the secretion of insulin from the pancreas, especially to enhance the stimulation of pancreatic β cell against glucose so as to release insulin; commonly used sulfonylurea blood glucose-lowering drug includes glibenclamide (trade name: Euglucon), glipizide (trade name: Minidiab) and gliclazide (trade name: Diamicron). However, in addition to its side-effects, such as rash and pruritus, its application to subject is also limited. For example, one that has severe liver and kidney dysfunction, pregnant women and nurses, and one that has severe sensitivity to sulfonylurea drug, are all not suitable to use this type of blood sugar-lowering drug.

(2) α-Glucosidase inhibitor: The main mechanism of this type of drug is to inhibit activities of pancreatic α-amylase and intra-intestinal α-glucosidase, and further inhibit the decomposition and absorption of carbohydrate in the intestinal tract. This type of drug can effectively lower the blood sugar after meal and insulin concentration, with side-effect of abdominal distention or occasional diarrhea, bellyache and nausea.

(3) Thiazolidinedione derivatives: The main action of this type of drug is to increase the activity of peroxisome proliferator-activated receptor (PPAR)-gamma in the cell nucleus, and further enhance the effect of insulin, such that glucose transfer protein GLUT2 and GLUT4 in the cell is increased so as to transport glucose into the cell for use. Commonly used one in clinic includes troglitazone (trade name: Rezulin), rosiglitazone (trade name: Avandia), pioglitazone (trade name: Actos) and the like. Among these, troglitazone induces lethal liver-toxicity, and therefore, it has been prohibited to be used two months after marketing in England in October 1997. Furthermore, in the USA, thiazolidinedione derivatives has been issued an order to withdraw comprehensively and to be forbid its use.

(4) Biguanides: This type of drug belongs to guanidine derivative. At present, biguanide blood sugar-lowering drug now is mainly metformin. This type of drug does not itself stimulate the secretion of insulin. Main mechanism in controlling blood sugar consists of following five points: a. Inhibiting appetite, and therefore is used preferably for obese type 2 diabetes patients to reduce their appetites, lower their body weight and further improve the peripheral action of insulin; b. Retarding the absorption of glucose by the intestinal tract; c. Promoting the anaerobic decomposition of glucose in the intestinal tract, and further increase the utilization of glucose in the intestinal tract, however, this may produce excess lactate that is susceptible to cause lactic acidosis; d. Enhancing the action of insulin in the liver, thereby inhibiting the neogenesis of glucose in the liver, and reduce the release of glucose from the liver; e. Promoting glucose transfer protein GLUT4 stored in the cell to move to the cell surface and to participate in the action of glucose transport, thereby increasing significantly the amount of glucose transfer protein on the cell surface. This type of blood sugar-lowering drug has some side-effects such as gastrointestinal discomfort in the first administration, for example anorexia, nausea, omitting, diarrhea and the like. A few may experience a skin rash, and after long-term use, inactivation phenomenon.

Probiotics are translated into many other names in Chinese and are defined by Food and Agriculture Organization of the United Nations (FAO) as live microorganisms and contains huge amounts of bacteria which can exert benefits on the host and help maintain their health. Majority of probiotics are lactic acid bacteria which can proliferate in the gut and produce lactic acid, acetic acid and short-chain fatty acids and exert a number of physiological functions. Among which, functions related to metabolic syndrome are described as follows: (1) Prevent diarrhea and constipation. Lactic acid and acetic acid can prevent invasion of foreign pathogens and proliferation of the spoilage bacteria, promote and maintain normal bowel movement and thus prevent diarrhea and constipation. (2) Regulate blood glucose level. Previous studies indicated that lactic acid bacteria can reduce blood glucose level and providing rats with sour milk daily containing probiotics for 8 weeks significantly reduces blood glucose level, glycosylated hemoglobin, OGTT and insulin levels in these rats. Administration of fermented milk containing probiotics also notably decreases blood glucose level in rats with diabetes induced by injection of streptozotocin (STZ). (3) Lower cholesterol and regulate blood lipids. Lactic acid bacteria may reduce cholesterol level by various mechanisms. The hydrolase activity of bile salt of the lactic acid bacteria allows cholesterol to be processed into conjugated bile salt during metabolism. When the bile salt binding activity increases, binding of cholesterol with conjugated bile salt results in co-precipitation and more cholesterol is precipitated and consequently contributes to the effect of cholesterol reduction. On the other hand, lactic acid bacteria can bond with cholesterol or even undergo of absorbed cholesterol and generate substances which are required by the cells. Among which, *Lactobacillus* has been shown to have better efficacy in cholesterol reduction. (4) Regulate blood pressure. Blood pressure-lowering substances are found in some fermented milk products, which is the best example of application of non-live probiotics in non-intestinal tract diseases. *L. helveticus* degrade lactoprotein during the process of fermentation and produce a number of peptides, among which VPP (Val-Pro-Pro) and IPP (Ile-Pro-Pro) can inhibit the activity of ACE. After intake of *L. helveticus*, the blood pressure of patients with high blood pressure is significantly lowered when compared with that before intake. (5) *Lactobacillus* can process free radicals through SOD or high concentration of Mn ions or reduce the toxicity of free radicals and $H_2O_2$ via glutathione. (6) Probiotics can reduce the expression of cytokines during the course of complicated inflammation. Mattar example: probiotics can increase the expression of Mucin 2 glycoprotein (MUC-2) in Caco-2 and reduce inflammation. In addition, studies conducted in cells indicated *Lactobacillus plantarum* 10hk2 can notably reduce the levels of inflammation-inducing cytokines such as interleukin-1β(IL-1β), interleukin-6 (IL-6) and tumor necrosis factor-α (TNF-α) and increase the level of the anti-inflammatory cytokine IL-10. (7) Certain bacteria in human intestinal tract such as *Lactobacillus* and *Bifidobacterium* can regulate symbiotic intestinal flora in the intestine through the intake of probiotics or supply nutrients.

Several literature or patents have suggested that feeding the diabetic rats with *Lactobacillus* can effectively prevent diabetes and lower blood glucose levels. Nonetheless, these published literature or patents on prevention of diabetes by *Lactobacillus* are limited to the controlling of blood glucose levels, body weight, blood lipid levels and cholesterol levels, and no further improvements are reported in prevention of other complications of diabetes such as inflammatory responses and declined liver function. Prior applications filed by the inventor of present invention indicates that *Lactobacillus reuteri* GMNL-89 can inhibit inflammatory responses (U.S. Pat. No. 7,901,926) and in U.S. Pat. No. 8,298,526, *Lactobacillus reuteri* GMNL-89 was found to efficiently improve the symptoms of type I diabetes under the disease model of type 1 diabetes. However, up to date, whether probiotics can effectively improve the symptoms of type 2 diabetes in the disease model of type 2 diabetes remains unclear.

SUMMARY OF THE INVENTION

One aspect of the invention is to provide a method for treating type 2 diabetes and its complications, comprising of administrating a probiotic composition, wherein the probiotic bacterial strain comprises of *Lactobacillus reuteri* GMNL-89 with the deposition numbers of BCRC 910340 and CCTCC M 207154.

According to the invention, the *Lactobacillus reuteri* GMNL-89 composition comprises of at least one of the following ingredients including live bacteria, dead bacteria and supernatant of bacterial cultures.

According to the invention, the composition is a pharmaceutical composition, food or their combinations thereof. Said pharmaceutical composition further comprises a pharmaceutically acceptable vehicle, wherein the inventive pharmaceutical composition is a dosage form for oral administration and the dosage form is selected from the group consisting of solutions, suspensions, emulsions, powders, tablets, pills, syrups, lozenges, troches, chewing gums, slurries and capsules.

According to the invention, the food further comprises at least one of the probiotic bacteria strain selected from the groups consisting of *Lactobacillus* sp., *Bifidobacterium* sp., *Streptococcus* sp. and yeasts. Additionally, the food further comprises of an edible material and said edible material comprises of water, fluid milk products, milk, concentrated milk, fermented milk, yogurt, sour milk, frozen yogurt, lactic acid bacteria-fermented beverages, milk powder, ice cream, cream cheese, dry cheese, soybean milk, fermented soybean milk, vegetable-fruit juices, juices, sports drinks, confectioneries, jellies, candies, infant formulas, health foods, animal feeds, Chinese herbs or dietary supplements.

According to another aspect of the invention, the complications of type 2 diabetes comprises of diabetic neuropathy, renal diseases, inflammation, cardiovascular complications, high cholesterol complications, eye diseases or liver diseases.

According to the invention, the pharmaceutical composition comprises of at least one of the following ingredients: a daily dose of $10^7$ to $10^9$ live *Lactobacillus reuteri* GMNL-89, $10^7$ to $10^9$ dead *Lactobacillus reuteri* GMNL-89 and supernatant of these bacterial cultures.

According to the invention, the food comprises of at least one of the following ingredients: a daily dose of $10^7$ to $10^9$ live *Lactobacillus reuteri* GMNL-89, $10^7$ to $10^9$ dead *Lactobacillus reuteri* GMNL-89 and supernatant of these bacterial cultures.

Another aspect of the invention is to provide a use of the composition for the manufacture of a medicament for the treatment of inhibiting high blood glucose level, high glycosylated hemoglobin ratio, high total cholesterol level, high liver triglyceride level, high low density lipoprotein (LDL) level, high homeostasis model assessment (HOMA) index, high tumor necrosis factor α (TNF-α), high Interleukin-1 β (IL-1β) or high interleukin-6 (IL-6), wherein the composition comprises of *Lactobacillus reuteri* GMNL-89 with a deposition number of CCTCC M 207154.

Still another aspect of the invention is to provide a use of the composition for the manufacture of a medicament for the treatment of increasing high density lipoprotein (HDL) level, the activity of superoxide dismutase (SOD) or the activity of glutathione peroxidase (GSH-Px), wherein the composition comprises of *Lactobacillus reuteri* GMNL-89 with a deposition number of CCTCC M 207154.

A further aspect of the invention is to provide a method of treating for inhibiting high blood glucose levels, high glycosylated hemoglobin ratios, high total cholesterol levels, high liver triglyceride concentrations, high low density lipoprotein (LDL), high homeostasis model assessment (HOMA) indicator, high tumor necrosis factor α (TNF-α), high Interleukin-1β(IL-1β) or high interleukin-6 (IL-6), comprising of administrating to a probiotic composition, wherein the probiotic bacterial strain comprises of *Lactobacillus reuteri* GMNL-89 with a deposition number of CCTCC M 207154.

According to another aspect, the invention provides a method of treating for increasing high density lipoprotein (HDL), the activity of superoxide dismutase (SOD) or the activity of glutathione peroxidase (GSH-Px), comprising administrating to a probiotic composition, wherein the probiotic bacterial strain comprises of *Lactobacillus reuteri* GMNL-89 with a deposition number of CCTCC M 207154.

According to still a further aspect, present invention provides a composition for the treatment of inhibiting high blood glucose level, high glycosylated hemoglobin ratio, high total cholesterol level, high liver triglyceride level, high low density lipoprotein (LDL) level, high homeostasis model assessment (HOMA) index, high tumor necrosis factor α (TNF-α), high Interleukin-1β(IL-1β) or high interleukin-6 (IL-6), wherein the composition comprises *Lactobacillus reuteri* GMNL-89 with a deposition number of CCTCC M 207154.

Another aspect of the invention is to provide a composition for the treatment of increasing high density lipoprotein (HDL) level, the activity of superoxide dismutase (SOD) or the activity of glutathione peroxidase (GSH-Px), wherein the composition comprises of the administration of *Lactobacillus reuteri* GMNL-89 with a deposition number of CCTCC M 207154.

At this stage of the study, STZ (10 mg/kg) and Nicotinamide (30 mg/kg) are used for generation of the disease model for type 2 diabetes by using high-fructose/high-fat diet to induce a hyperglycemic obese animal model for investigation of the effects of live GMNL-89, heat-killed GMNL-89 and supernatant of live GMNL-89 bacterial culture on insulin resistance, blood glucose stability and body weight. 1. Examination of the effects of live GMNL-89, heat-killed GMNL-89 and supernatant of live GMNL-89 bacterial cultures on the activities of anti-oxidation enzymes and inflammatory indicators in this animal model. 2. Investigation of the effects of dietary supplement of live GMNL-89, heat-killed GMNL-89 and supernatant of live GMNL-89 bacterial cultures on insulin resistance and blood glucose level in this animal model. 3. Analysis of the effects of dietary supplement of live GMNL-89, heat-killed GMNL-89 and supernatant of live GMNL-89 bacterial cultures on blood LDL, TG, TC and HDL levels in this animal model. 4. Inspection of the effects of dietary supplement of live GMNL-89, heat-killed GMNL-89 and supernatant of live GMNL-89 bacterial cultures on energy metabolism and study its underlying mechanism(s).

These features and advantages of the present invention will be fully understood and appreciated from the following detailed description of the accompanying Drawings.

BRIEF DESCRIPTION OF THE DRAWINGS

*indicates significant difference was found when compared with the diabetic group, P<0.05.

DETAILED DESCRIPTION OF THE PREFERRED EMBODIMENT

Unless defined otherwise, all technical and scientific terms used herein have the meaning commonly understood by a person skilled in the art to which this invention belongs. As used herein, the following terms have the meanings ascribed to them unless specified otherwise. The present invention will now be described more specifically with reference to the following embodiments, which are provided for the purpose of demonstration rather than limitation.

Present invention features a composition and use of probiotics for treating type 2 diabetes, wherein the probiotic bacteria comprises of at least one of the following contents: live bacteria, dead bacteria and supernatant of the bacterial cultures of *Lactobacillus reuteri* GMNL-89 with the deposition numbers of BCRC 910340 and CCTCC M 207154 and a pharmaceutically acceptable vehicle. In addition, the invention also features a novel use of said composition or said *Lactobacillus* in treating type 2 diabetes. *Lactobacillus reuteri* GMNL-89 is deposited in China center for Type Culture Collection (CCTCC) with the deposit number CCTCC M 207154 on Nov. 19, 2007. CCTCC address: HongShan Qu Ba Yi Avenue, Wuhan, Hubei, 430072, P.R.China.

The *Lactobacillus* isolate of the invention also include its subcultures or mutants, which still maintain the same characteristics, genomes or uses (for treating type 2 diabetes) of the strain.

According to the invention, the composition comprises of the following materials, but are not limited to: foods, drinks, healthy foods, additives for animal drinking water, additives for animal feeds, medical compositions for human and animal uses, food additives, and drink additives and any other forms suitable for use in the invention.

The term "treatment", "under treatment" and other similar terms refer to methods that ameliorate, improve, reduce or reverse the disease or symptoms relating to the disease which is affecting the patient as well as the methods that prevent the occurrence of a disease or any disease-related symptoms.

The term "pharmaceutically acceptable" is used herein to refer to a material or composition which shall be compatible with other ingredients in the formulation and is harmless to a patient.

The term "diabetes-related complications" as used herein refer to the following diseases, but are not limited to, diabetic neuropathy (including, but is not limited to, bladder weakness, bloating, constipation, diarrhea, impotence, loss of sensation), kidney disease (including, but is not limited to, glomerular nephritis, glomerular sclerosis, nephrotic syndrome, hypertensive nephrosclerosis, end-stage renal disease, uremia), inflammation, cardiovascular, or high cholesterol complications (including, but is not limited to, stroke, myocardial infarction, coronary thrombosis, angina, heart failure, cardiac instability, poor peripheral circulation, foot infections, etc.), eye diseases (including, but is not limited to, retinopathy, cataracts, glaucoma, low vision (poor eyesight)), liver disease (including, but is not limited to, liver fibrosis, fatty liver, non-alcoholic fatty liver, and cirrhosis).

The inventive composition can be formulated into a dosage form suitable for use in the invention through isolation of the abovementioned *Lactobacillus* by using techniques known to the person skilled in the art and mixed with a pharmaceutically acceptable vehicle. The excipient included in the inventive composition consists of, but is not limited to, solution, suspension, emulsion, powder, tablet, pill, lozenge, troche, chewing gum, slurry and other similar or suitable dosage forms for use in the invention.

The pharmaceutically acceptable vehicle of the inventive composition contains one or more of the following reagents comprising of solvent, emulsifier, suspending agent, decomposer, binding agent, excipient, stabilizing agent, chelating agent, diluent, gelling agent, preservative, lubricant, surfactant and any other similar or suitable reagents for use in the invention.

Moreover, one or more of the common solubility-increasing agents, buffering agents, preservatives, coloring agents, fragrances, spices and flavoring agents may be added, in adequate amount, to the abovementioned composition if needed.

In another example of the invention, the composition provided herein can be manufactured as a food product or health product by addition of an edible material. Said edible material includes, but is not limited to, water, fluid milk products, milk, concentrated milk, fermented milk, yogurt, sour milk, frozen yogurt, lactic acid bacteria-fermented beverages, milk powder, ice cream, cream cheese, dry cheese, soybean milk, fermented soybean milk, vegetable-fruit juices, juices, sports drinks, confectioneries, jellies, candies, infant formulas, health foods, animal feeds, Chinese herbs and dietary supplements.

In addition, the novel bacterial strain discovered in the invention can also be included in a composition along with other known bacterial strains.

The inventive composition may further include at least one of the following groups of known probiotic strains: *Lactobacillus* sp., *Streptococcus* sp., *Bifidobacterium* sp., and yeasts.

Furthermore, the known *Lactobacillus* sp. include, but are not limited to, *Lactobacillus lactis*, *Lactobacillus acidophilus*, *Lactobacillus helveticus*, *Lactobacillus bifidus*, *Lactobacillus casei*, *Lactobacillus paracasei* subsp. *paracasei*, *Lactobacillus rhamnosus*, *Lactobacillus gasseri*, *Lactobacillus reuteri* and *Lactobacillus fermentum* or their combinations thereof.

The known *Streptococcus* sp. include, but are not limited to, *Streptococcus lactis*, *Streptococcus thermophilus*, *Streptococcus cremoris* or their combinations thereof.

The known *Bifidobacterium* sp. include, but are not limited to, *Bifidobacterium breve*, *Bifidobacterium lactis*, *Bifidobacterium longum*, *Bifidobacterium bifidum* or their combinations thereof.

The known yeasts include, but are not limited to, *Saccharomyces cereviseae*, *Candida kefyr*, *Saccharomyces florentinus* or their combinations thereof.

In addition, the invention also provides a method for preparation or use of a composition comprising the abovementioned *Lactobacillus* strains for treating type 2 diabetes.

In the invention, the administering routes of the composition and the method of its use for reducing or maintaining body weight can be adjusted according to various needs and are not specified and the preferred method is oral administration of a suitable dosage form of the composition.

The present invention will now be described more specifically with reference to the following embodiments, which are provided for the purpose of demonstration rather than limitation Materials and Methods A Grouping, Feed and Care of the Study Animals Nine-week-old Male SD rats (180±20 g) purchased from BioLASCO Taiwan Co., Ltd. are randomly assigned to 7 groups. The number of groups and rats of each group are described as follows:
1. Normal control group: n=5
2. Diabetic group: n=5
3. Diabetic+dead bacteria (DB) group: n=8
4. Diabetic+Low dose live bacteria (LLB) group: n=8
5. Diabetic+High dose live bacteria (HLB) group: n=8
6. Diabetic+Low dose supernatant of live bacterial culture (LS) group: n=8
7. Diabetic+High dose supernatant of live bacterial culture (HS) group: n=8

B Feeding Dosage Calculations:
(1) Intake of test samples and induction of hyperglycemia are performed simultaneously.
(2) Each experimental group: daily tube feeding of the rats in live bacteria group, dead bacteria group and supernatant of live bacterial culture groups with lactic acid bacteria products at various concentrations from one week after arrival to the day of scarification. Preparation of dead bacteria is by autoclave of the bacteria at 121° C. for 15 minutes followed by freeze-dried of the bacterial culture into bacterial powder. Preparation of supernatant of live bacteria is through centrifugation of the bacterial culture at 4000 rpm for 20 minutes followed by filtration of the supernatant of lactic bacteria culture via a 0.22 μm filter membrane. A protein assay kit is then utilized to determine the protein concentration of the supernatant and the protein concentration of the supernatant is then adjusted to 100 μg/ml and 20 μg/ml.
(3) Upon reaching the target blood glucose level, the rats are subjected to the tests required (the target blood glucose level is 200 mg/dL as indicated in the Flow chart).
(4) Solvent without lactic acid in the same volume is used to treat normal and diabetic groups.

Feed dose of each group is described as follows:
1. Normal control group:
2. Diabetic group:
3. Diabetic+DB group: tube feeding of $1.6 \times 10^8$ CFU (0.04 g) dead GMNL-89/per day
4. Diabetic+LLB group: tube feeding of $1.6 \times 10^7$ CFU (0.004 g) live GMNL-89/per day
5. Diabetic+HLB group: tube feeding of $1.6 \times 10^8$ CFU (0.04 g) live GMNL-89/per day
6. Diabetic+LS group: 20 μg total protein/mL and 1 mL/rat/per day
7. Diabetic+HS group: 100 μg total protein/mL and 1 mL/rat/per day C Animal Fee Formulation and Methods of Administration:

Each rat was given 30 g of feed per day and the formula of the feeds are described as follows:

TABLE 1

Diet formulation, purchased from Harlan

| AIN93M feed ingredients | General feed ratio (g) | High oil high fructose feed ratio (g) |
| --- | --- | --- |
| Corn starch | 16.30 | 1.58 |
| Dextrin | 5.43 | 5.25 |
| Casein-vitamin free | 4.9 | 4.9 |
| Sucrose | 3.50 | 9.8 |
| Fructose | 0.00 | 7.00 |
| Powdered cellulose | 1.75 | 1.65 |
| Soybean Oil | 1.4 | 7.7 (pork fat) |
| AIN 93M Mineral Mix | 1.23 | 1.23 |
| AIN 93 Vitamin Mix | 0.4 | 0.4 |
| Choline Bitartrate | 0.07 | 0.07 |
| L-Cystine | 0.063 | 0.063 |
| t-Butylhydroquinone | 0.28 (mg) | 0.28 (mg) |
| Kcal/30 g/(day) | 133 | 167 |

D Creation of a Type 2 Diabetes Disease Animal Model:

Normal control group and diabetic group is designed and the rats in the diabetic group are given a high-carbohydrate/high-fat diet and received intraperitoneal injections of low-dose streptozotocin (STZ, 10 mg/kg) and Nicotinamide (30 mg/kg) every two days during the course of the study. The blood glucose level of the rats elevated to >180 mg/dL indicates successful creation of the disease.

E Oral Glucose Tolerance Test (OGTT)

Oral administration of the study animals with glucose (1 g/kg) and collect their blood samples at 30, 60, 90, 120 and 180 minutes before and after glucose administration. Rat Glucose Assay Kit is used to determine blood glucose levels.

F Blood Biochemical Tests

Blood was collected from the vein and immediately centrifuged at 3000 rpm (1630×g) for 20 minutes. The upper layer serum is collected for the following biochemical analyses:

1. Glycated Hemoglobin (HbA1c)

Add 100 µL sample and incubate at 37° C. for 2 hrs. Add 100 µL detection reagent A (prepared immediately before use) and incubate 37° C. for 1 hr followed by addition of 100 µL detection reagent B (prepared immediately before use) and incubate at 37° C. for another 1 hr. Add Substrate Solution (90 µL) and incubate at 37° C. in dark for color development for 15-30 minutes. Add 50 µL Stop Solution to stop the reaction. Use a spectrophotometer to measure the absorbance at 450 nm and calculate HbA1c concentrations in the blood by using the standard curve equation.

2. Measurement of Glucose Level

An aliquot of 20 µL of the serum obtained after blood collection is mixed with glucose and blood glucose level is determined by using the Rat Glucose Assay Kit. Reagent solution in the amount of 3 mL are mixed with sample and incubated at 37° C. for 5 minutes. The absorbance of the sample is measured at 500 nm using a spectrophotometer which is then converted into the serum glucose level.

3. Measurement of Insulin Level

The absorbance of an aliquot of 0.5 µL of the blood sample is examined by using the Rat Insulin Assay Kit and insulin concentration is obtained by comparing with the concentrations of the standard curve.

4. Measurement of Triglyceride (TG) Level

An aliquot of 10 µL of the serum obtained after blood collection is mixed with 1 mL of the test solution in the Triglyceride Enzymatic kits and incubated at 37° C. for 5 minutes. The absorbance of the sample is measured at 546 nm using a spectrophotometer which is then converted into the serum triglyceride level. The equation for conversion is shown as follows:

$$\text{Plasma Triglyceride} = (Es - \text{Blank})/(Estd - \text{Blank}) \times 200$$

Es: absorbance of the blood sample
Estd: absorbance of the standard solution
Blank: absorbance of the kits without samples
200: Concentration of the standard solution, 200 mg/dL 5. Measurement of Total Cholesterol (TC) Level An aliquot of 10 µL of the serum obtained after blood collection is mixed with 1 mL of the test solution in the Cholesterol Enzymatic kits and incubated at 37° C. for 5 minutes. The absorbance of the sample is measured at 500 nm using a spectrophotometer which is then converted into the serum cholesterol level. The equation for conversion is shown as follows:

$$\text{Plasma TC} = (Es - \text{Blank})/(Estd - \text{Blank}) \times 200$$

Es: absorbance of the blood sample
Estd: absorbance of the standard solution
Blank: absorbance of the kits without samples
200: Concentration of the standard solution, 200 mg/dL 6. Measurement of High Density Lipoprotein (HDL) Level An aliquot of 10 µL of the serum obtained after blood collection is mixed with 1 mL of the test solution in the High Density Lipoprotein Enzymatic kits and incubated at 37° C. for 5 minutes. The absorbance of the sample is measured at 500 nm using a spectrophotometer which is then converted into the serum HDL level. The equation for conversion is shown as follows:

$$\text{Plasma HDL} = (Es - \text{Blank})/(Estd - \text{Blank}) \times 200$$

Es: absorbance of the blood sample
Estd: absorbance of the standard solution
Blank: absorbance of the kits without samples
200: Concentration of the standard solution, 200 mg/dL 7. Measurement of low density lipoprotein (LDL) level An aliquot of 50 µL of the serum obtained after blood collection is mixed with 1 mL of the test solution in the Low Density Lipoprotein Enzymatic kits and incubated at 37° C. for 5 minutes. The absorbance of the sample is measured at 500 nm using a spectrophotometer which is then converted into the serum HDL level. The equation for conversion is shown as follows:

$$\text{LDL-C} = TC - (A\,\text{sample} \times 1265)$$

G. Studies on Cytokine Secretion

After feeding the animals with test materials for 8 consecutive weeks, serum was collected from the rats and the concentrations of cytokines secreted were detected by Enzyme Linked Immunosorbent Assays (ELISA) so as to examine the differences between the experimental and control group. Add 100 µL diluted capture antibodies (per well) onto 96-well plates and incubate overnight at 4° C. Discard the supernatant the next day and wash 4 times with wash solution followed by addition of 200 µL blocking solution (per well). Incubate the plates at room temperature for 2 hrs, discard the supernatant, wash 4 times with wash solution, add 100 µL diluted HRP-conjugated detection antibodies and incubate at room temperature for 30 minutes. Discard the supernatant, wash 5 times with wash solution, add 100 µL enzyme substrate solution and incubate in dark for 30 minutes at room temperature. Add 100 µL stop solution to each well and measure the absorbance at 450 nm.

H. Measurement of Superoxide Dismutase (SOD) Level

According to the method developed by Beutlerin 1975, the principle of this enzyme determination method is xanthine is catalyzed by XOD and produces uric acid and superoxide radical which then interact with 4-iodophenyl-3-(-4-nitrophenol)-5-phenyl tetrazolium (I.N.T) and results in red formazan dye. The activity of the enzyme is assessed by the amount of superoxide anion eliminated by SOD in this reaction. At 37° C., add 0.05 mL serum and 1.70 mL mixed substrate (0.05 mmol/L, 0.025 mmol/L I.N.T) to 0.25 mL xanthine oxidase (80 U/L), mix well, and measure the changes of the absorbance at 505 nm for 3 minutes and compare the results with the standards.

I. Measurement of Malondialdehyde (MDA) Level

The method used in this study for analysis of MDA is developed by Yagi in 1984 and the improvements made by Prasad et al. in 1992 are also adopted and are described as follows: MDA is the end product of lipid peroxidation and reaction of MDA with thiobarbituric acid (TBA) yields a red thiobarbituric acid reactive substances (TBARS). The content of MDA is then measured at 515 nm (excitation) and 553 nm (emission) using a fluorescence spectrophotometer. On the other hand, hydrolysis of 1,1,3,3-tetra-methoxy-propane (TMP) in acids generates MDA and thus TMP is used as standards to calculate MDA level in tissues as an indicator of lipid peroxidation. First, 1 mL of plasma was added to 1 mL 10% trichloroacetic acid (TCA) with vigorous shaking and centrifuged at 1500×g for 10 minutes and 1 mL of the upper layer solution or various standard solutions was added to 1 mL TBA solution and 0.1 mL dibutyl hydroxy toluene (BHT) solution with vigorous shaking followed by incubation in a 95° C. water bath for 60 minutes. Add 2 mL butanol with vigorous shaking to samples after cooling down and centrifuge at 1500×g for 10 minutes. Supernatant was collected and absorbance was measured by fluorescence spectrophotometer at 515 nm excitation/553 nm emission.

J. Determination of Glutathione Peroxidase (GSH-Px) Level

The methods presented by Paglia et al. in 1967 and modified by Lawrence et al. in 1976 were utilized to measure the activity of GSH-Px. The principle of these methods is GSH-Px oxidizes glutathione (GSH) to oxidized glutathione (GSSG) in the presence of cumene hydroperoxide and GSSG will then be reduced to GSH again by Glutathione reductase (GR) at the cost of NADPH. Therefore, at 340 nm, measurement of the consumption of NADPH can give the activity of GSH-Px through reduction of absorbance. At 37° C., mix 0.05 mL serum with 0.10 mL cumene hydroperoxide and measure the absorbance at 340 nm.

Example 1

Confirmation of Creation of the Animal Disease Model

Figure 1:
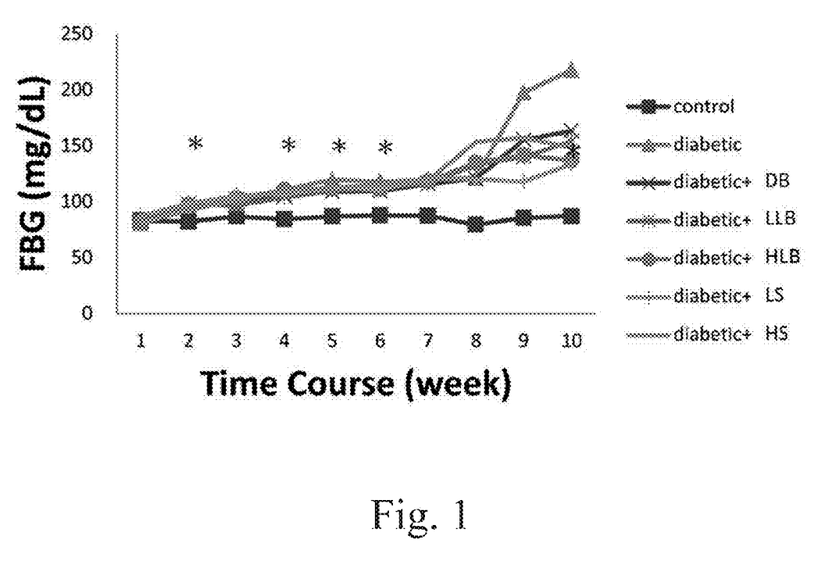
FIG. 1 shows the fasting blood glucose (FBG) levels of rats feeding with GMNL-89 dead bacteria (DB), low dose live bacteria (LLB), high dose live bacteria (HLB), low dose supernatant (LS) and high dose supernatant (HS) for 10 weeks during the course of the study. *indicates significant difference was found when compared with the diabetic group, P<0.05.
Figure 2:
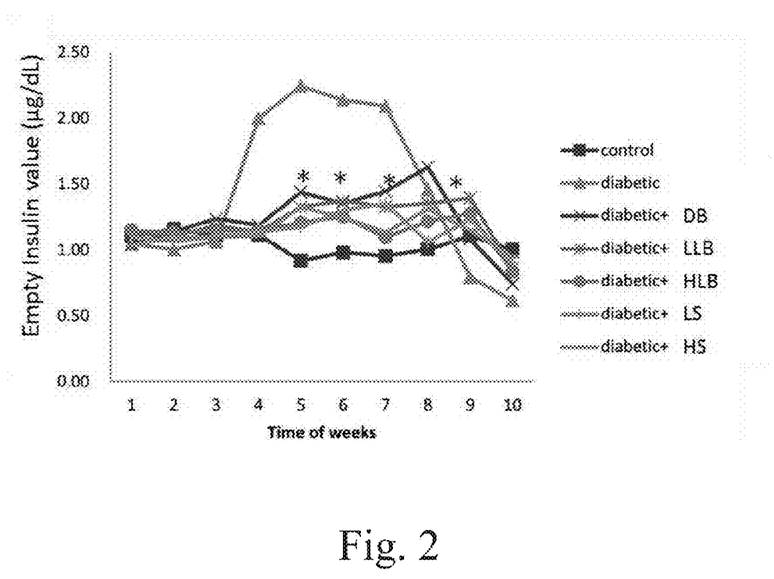
FIG. 2 shows the fasting insulin levels of rats feeding with GMNL-89 dead bacteria (DB), low dose live bacteria (LLB), high dose live bacteria (HLB), low dose supernatant (LS) and high dose supernatant (HS) for 10 weeks during the course of the study. *indicates significant difference was found when compared with the diabetic group, P<0.05.

The fasting blood glucose levels between the experimental groups and the type 2 diabetic group showed no significant differences for the first 7 weeks. However, the blood glucose levels in diabetic, high/low live bacteria and high supernatant groups started to rise at the eighth week, but the rising trend is more moderate in dead bacteria, high/low live bacteria and high supernatant groups. The supernatant groups showed the best protection against STZ+Nicotinamide induced type 2 diabetes in the animal model during the first eight weeks. Likewise, similar results were also observed after 10 weeks of the experiment. Alternatively, the fasting insulin level in the diabetic group began to rise at the fourth week demonstrating a compensatory phenomenon, indicating the rats in the diabetic group already had problems of insulin production at the fourth week. In contrary, the fasting insulin level in all groups fed with different lactic acid bacteria remain stable, suggesting secretion of insulin and utilization of carbohydrates are within normal ranges in these rats. Based on the results shown in FIG. 1 and FIG. 2, rats created under this animal disease model developed insulin resistance at week 6 and hyperglycemia phenomenon appeared at week 8, but groups receiving lactic acid bacteria in their feeds showed only moderate increase of blood glucose levels. Fasting blood glucose levels (FIG. 1) and insulin levels (FIG. 2) in DB, LLB, HLB, LS and HS groups all demonstrate significant differences when compared with the diabetic group.

Example 2

Documentation of Daily Intake

During the course of the study, daily intake of diet was recorded and averaged. Because the differences in daily intake of the rats may affect their body weights and consequently have an effect on the results, the intake amount in each group was recorded and no statistically significant difference was found when compared with the amount in the diabetic group. In summary, intake calories of each group are similar and have no effects on the study results.

TABLE 2

Average intake amount in rats of each group during the course of the study (g)

| Intake amount | Group | | | | | | |
|---|---|---|---|---|---|---|---|
| | Control group | Diabetes | Diabetes + dead bacteria | Diabetes + low live bacteria | Diabetes + high live bacteria | Diabetes + low supernatant | Diabetes + high supernatant |
| Intake amount (g) | 27.2 ± 4.5 | 23 ± 4.4 | 22 ± 5.3 | 22.2 ± 5 | 23.5 ± 5 | 22.4 ± 4.6 | 21.8 ± 4.9 |

Example 3

Body Weight and the Weights of Liver and Kidney

In addition to recording the intake amount of daily diet, weekly body weight change was also documented. From Table 3, no statistically significant differences of body weights were found between the rats of various groups and the diabetic group. At week 10, these rats were sacrificed and their livers and kidneys were collected and weighed. Likewise, according to the results (Table 4), no statistically significant differences of the organ weights were observed in different groups of rats when compared with the rats in the diabetic group.

TABLE 3

Body weight changes in rats of each group during the course of the study (g)

| Week | Group | | | | | | |
|---|---|---|---|---|---|---|---|
| | Control group | Diabetes | Diabetes + dead bacteria | Diabetes + low live bacteria | Diabetes + high live bacteria | Diabetes + low supernatant | Diabetes + high supernatant |
| Week 1 | 406 ± 34 | 425 ± 25 | 400 ± 13 | 403 ± 10 | 400 ± 26 | 429 ± 29 | 426 ± 13 |
| Week 2 | 424 ± 29 | 439 ± 40 | 410 ± 36 | 415 ± 35 | 420 ± 34 | 436 ± 35 | 411 ± 28 |
| Week 3 | 432 ± 33 | 454 ± 40 | 413 ± 42 | 417 ± 40 | 440 ± 39 | 446 ± 36 | 437 ± 33 |
| Week 4 | 450 ± 35 | 481 ± 45 | 439 ± 47 | 445 ± 48 | 459 ± 29 | 467 ± 37 | 457 ± 36 |

TABLE 3-continued

Body weight changes in rats of each group during the course of the study (g)

| | Group | | | | | | |
|---|---|---|---|---|---|---|---|
| Week | Control group | Diabetes | Diabetes + dead bacteria | Diabetes + low live bacteria | Diabetes + high live bacteria | Diabetes + low supernatant | Diabetes + high supernatant |
| Week 5 | 480 ± 38 | 513 ± 45 | 442 ± 57 | 460 ± 58 | 483 ± 45 | 489 ± 39 | 483 ± 45 |
| Week 6 | 480 ± 37 | 509 ± 19 | 428 ± 89 | 455 ± 59 | 487 ± 40 | 493 ± 36 | 483 ± 49 |
| Week 7 | 493 ± 59 | 543 ± 57 | 461 ± 70 | 481 ± 66 | 508 ± 45 | 513 ± 26 | 505 ± 53 |
| Week 8 | 496 ± 59 | 559 ± 65 | 469 ± 79 | 498 ± 52 | 519 ± 41 | 520 ± 28 | 511 ± 60 |
| Week 9 | 510 ± 69 | 529 ± 108 | 461 ± 90 | 506 ± 55 | 529 ± 40 | 536 ± 28 | 523 ± 63 |
| Week 10 | 506 ± 76 | 570 ± 78 | 465 ± 88 | 511 ± 58 | 524 ± 37 | 533 ± 29 | 519 ± 64 |

TABLE 4

The weights of livers and kidneys of rats in each group (g)

| | Group | | | | | | |
|---|---|---|---|---|---|---|---|
| Organ | Control group | Diabetes | Diabetes + dead bacteria | Diabetes + low live bacteria | Diabetes + high live bacteria | Diabetes + low supernatant | Diabetes + high supernatant |
| Liver | 13.21 ± 1.4 | 18.88 ± 0.7 | 17.72 ± 5.1 | 18.33 ± 3.4 | 17.73 ± 1.9 | 18.25 ± 4.5 | 17.56 ± 2.6 |
| Kidney | 2.91 ± 0.1 | 3.32 ± 0.5 | 3.18 ± 0.4 | 3.16 ± 0.3 | 3.07 ± 0.4 | 3.38 ± 0.2 | 3.16 ± 0.2 |

Example 4

Serum Biochemical Analyses

From the results of Table 5, TC, TG and HbA1c levels in groups received lactic acid bacteria treatments are significantly lower when compared with the diabetic group. From the perspectives of individual group, change of TC levels is DB>LLB>HLB>HS>LS and similar trend can also be observed for TG levels. Hence, feeding of lactic acid bacteria is effective in reduction of TG and total cholesterol levels and the effects vary along with the concentrations of the bacteria. However, lactic acid bacteria have different effects on blood glucose control. The change of HbA1c levels showed DB>LLB>LS>HLB>HS. In spite of the fact that lactic acid bacteria can reduce blood total cholesterol, triglyceride and HbA1 levels, the effects of each treatment on each group are different. Further examination suggests that though the effects of HS treatment on regulation of TG, TC and HbA1c levels are not as dramatic, it has significant effects on reduction of the levels of all biochemical indicators. The Homeostasis model assessment (HOMA) is an indicator for assessing insulin resistance and the higher the value, the poor the insulin utilization. The HOMA indicator of LH group at week 7 is the lowest and the HLB as well as HS groups have the best HOMA performance.

TABLE 5

The levels of serum biochemical indicators in rats of each group at week 8

| | Group | | | | | | |
|---|---|---|---|---|---|---|---|
| Week | Control | Diabetes | Diabetes + dead bacteria | Diabetes + low live bacteria | Diabetes + high live bacteria | Diabetes + low supernatant | Diabetes + high supernatant |
| TC | *68.9 ± 1.2 | 102.0 ± 2.1 | *93.0 ± 2.5 | *91.2 ± 2.1 | *89.0 ± 2.5 | *82.5 ± 2.7 | *84.3 ± 2.4 |
| TG | *85.8 ± 1.9 | 210.6 ± 2.2 | *131.4 ± 2.6 | *101.0 ± 3.5 | *99.3 ± 5.1 | *92.5 ± 3.8 | *91.0 ± 4.6 |
| LDL | *16.0 ± 1.1 | 22.3 ± 0.4 | *20.0 ± 0.5 | 21.1 ± 0.6 | 20.6 ± 1.2 | *18.2 ± 0.3 | *16.8 ± 0.5 |
| HDL | *40.0 ± 0.5 | 34.0 ± 0.9 | 35.8 ± 1.1 | 35.6 ± 0.8 | 36.2 ± 0.7 | 36.1 ± 1.1 | *36.8 ± 0.8 |
| HbA1c | *4.8 ± 0.2 | 6.6 ± 0.3 | *5.5 ± 0.2 | *5.4 ± 0.2 | *5.1 ± 0.2 | *5.2 ± 0.3 | *5.0 ± 0.2 |
| HOMA (Week 7) | 3.7 | 11.1 | 7.4 | 6.9 | 5.8 | 7.1 | 6 |

1. HOMA-IR = fasting serum insulin level (mmol/L) × fasting serum glucose level (ug/L)/22.5
2. *The difference is significant when compared with the rats in the diabetic group, P < 0.05.

Example 5

Oral Glucose Tolerance Test (OGTT) and Change in Blood Glucose (ΔAUC)

Figure 3:
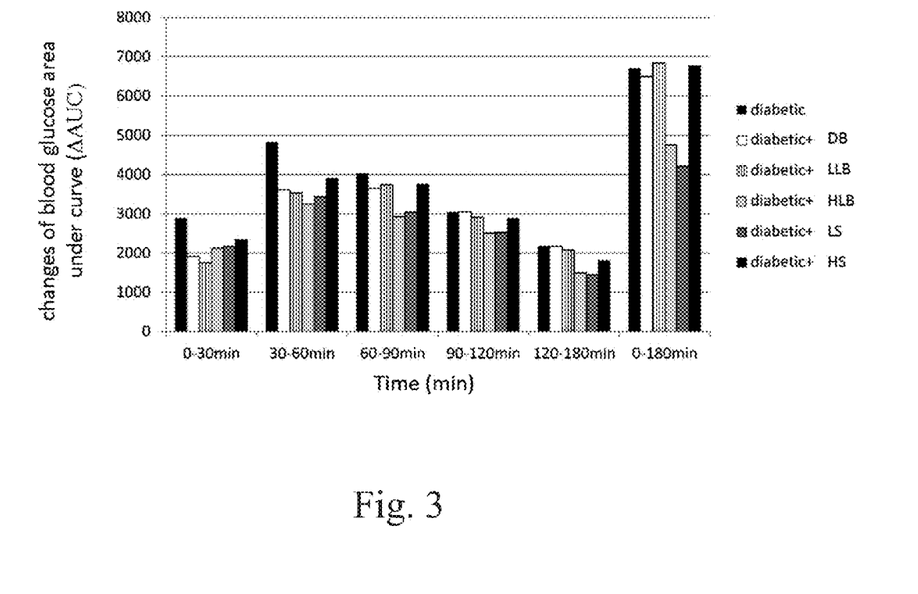
FIG. 3 shows ΔAUC data analysis results of type 2 diabetes rats feeding with GMNL-89 dead bacteria (DB), low dose live bacteria (LLB), high dose live bacteria (HLB), low dose supernatant (LS) and high dose supernatant (HS) for 6 weeks.
Figure 4:
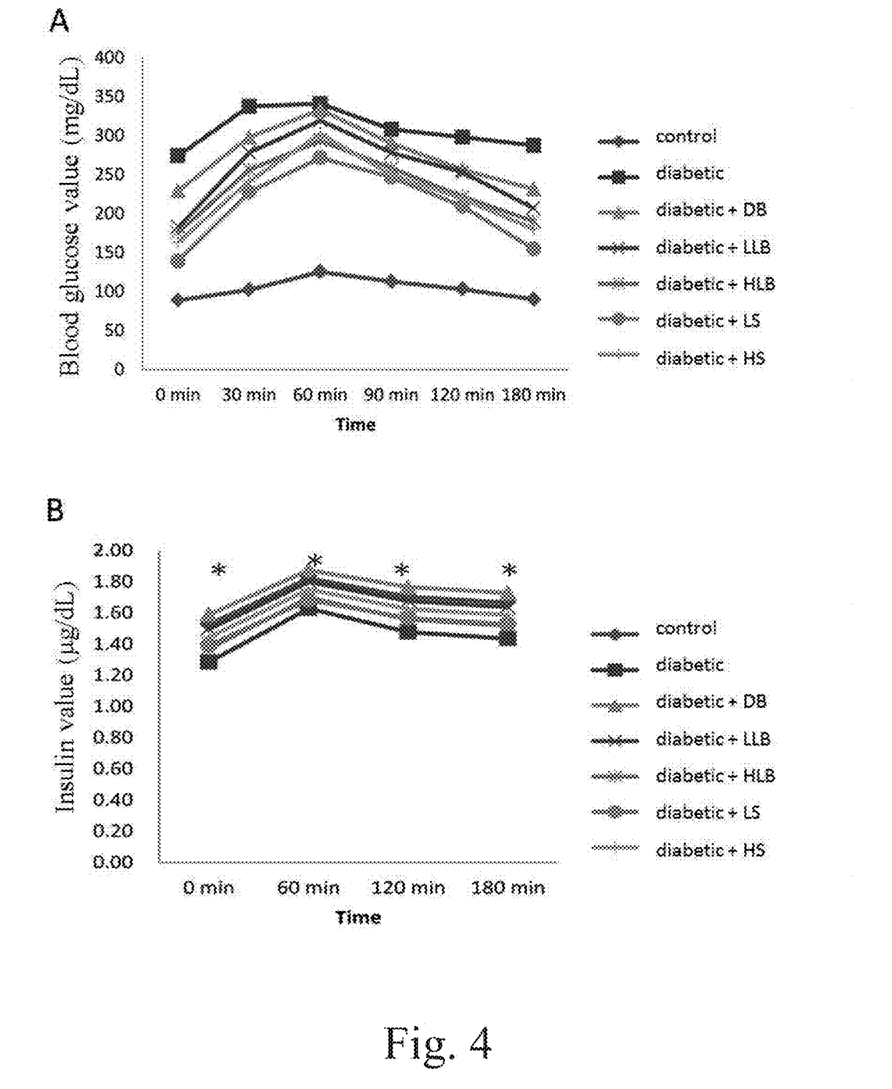
FIG. 4 shows the effects on glucose tolerance in type 2 diabetes rats feeding with GMNL-89 dead bacteria (DB), low dose live bacteria (LLB), high dose live bacteria (HLB), low dose supernatant (LS) and high dose supernatant (HS) for 8 weeks. A: OGTT data analysis of each rat group; B: Change of insulin levels within 0-180 minutes in rats of each group.
Figure 5:
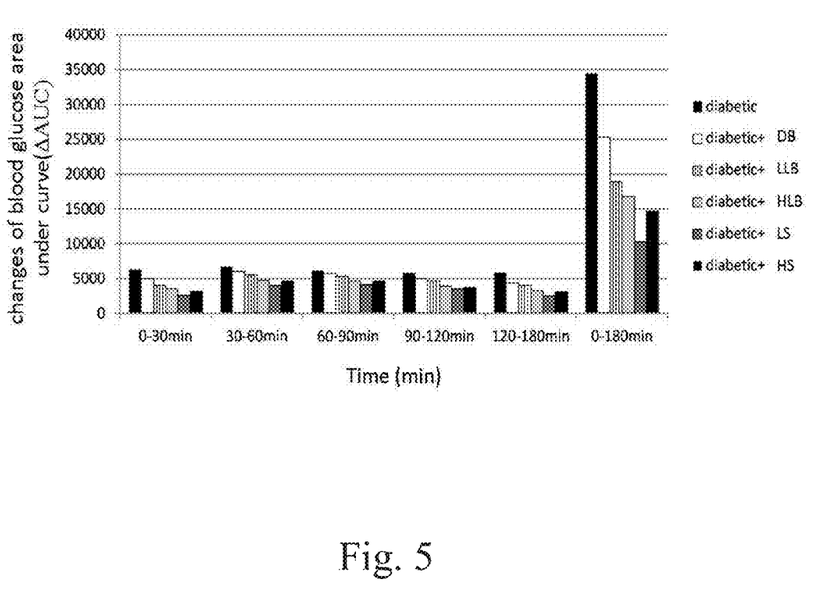
FIG. 5 shows ΔAUC data analysis results of type 2 diabetes rats feeding with GMNL-89 dead bacteria (DB), low dose live bacteria (LLB), high dose live bacteria (HLB), low dose supernatant (LS) and high dose supernatant (HS) for 8 weeks.

The first oral glucose resistance test was conducted at week 8. From the OGTT results obtained at week 8, LS>HS and HLB>LLB (FIG. 4). For insulin levels (FIG. 4B), all treatment groups including DB, LLB, HLB, LS and HS groups show significant differences when compared with the diabetic group. Similar results are also found for ΔAUC (FIG. 3 and FIG. 5).

Example 6

Secretion of Inflammatory Cytokines

The rats were sacrificed at week 10 and their blood was collected for assessing the levels of inflammatory cytokines. According to Table 6, rats fed with lactic acid bacteria show notably reduction of these inflammatory indicators. In particular, it is more evident in the LH group and therefore feeding of lactic acid bacteria is helpful for decrease of inflammatory responses.

TABLE 6

Anti-oxidative enzyme activity in rats of each group

| Enzyme | Control | Diabetes | Diabetes + dead bacteria | Diabetes + low live bacteria | Diabetes + high live bacteria | Diabetes + low supernatant | Diabetes + high supernatant |
|---|---|---|---|---|---|---|---|
| SOD (U/ml) | *0.18 ± 0.02 | 0.09 ± 0.01 | *0.15 ± 0.01 | *0.10 ± 0.02 | *0.15 ± 0.01 | *13 ± 0.01 | *0.14 ± 0.02 |
| TBARS (μm) | *43.5 ± 0.8 | 62.2 ± 0.8 | *39.2 ± 0.8 | *56.9 ± 1.0 | *58.8 ± 1.1 | *35.9 ± 1.1 | *14.9 ± 1.0 |
| GPx (nmol/min/ml) | *45.1 ± 0.7 | 6.1 ± 0.8 | *12.2 ± 0.9 | *45.8 ± 0.8 | *44.1 ± 1.1 | *28.8 ± 0.9 | *41.5 ± 1.0 |

*The difference is significant when compared with the rats in the diabetic group, $P < 0.05$.

Example 7

Anti-Oxidative Enzyme Activity

The rats are sacrificed at week 10 and their blood are collected for evaluation of the activity of anti-oxidative enzymes. According to the results shown in Table 7, feeding the rats with various lactic acid bacteria ingredients have different effects on the activity of anti-oxidative enzymes. For example, when compared with the diabetic group, the activities of SOD and GPx increased significantly in the rats fed with lactic acid bacteria, while TBARs reduced dramatically. On the other hand, after administration of various lactic acid bacteria treatments, decrease of the oxidative stress in these rats may be due to increased anti-oxidative activity of the SOD and GPx.

TABLE 7

Secretion of inflammatory cytokines in rats of each group

| Week | Control | Diabetes | Diabetes + dead bacteria | Diabetes + low live bacteria | Diabetes + high live bacteria | Diabetes + low supernatant | Diabetes + high supernatant |
|---|---|---|---|---|---|---|---|
| TNF-α (pg/ml) | *63.4 ± 1.0 | 72.9 ± 4.7 | *34.5 ± 0.8 | *56.4 ± 1.1 | *47.4 ± 1.0 | *11.6 ± 0.8 | *24.4 ± 1.0 |
| IL-1β (pg/ml) | *106.5 ± 1.0 | 233.5 ± 1.0 | *67.9 ± 1.5 | *99.6 ± 1.3 | *111.7 ± 1.5 | *54.5 ± 1.0 | *56.7 ± 0.7 |
| IL-6 (pg/ml) | *228.5 ± 1.1 | 1213.7 ± 1.0 | *237.6 ± 1.0 | *214.4 ± 0.6 | *217.5 ± 1.0 | *233.7 ± 0.7 | *275.3 ± 1.1 |

*The difference is significant when compared with the rats in the diabetic group, $P < 0.05$.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for treating type 2 diabetes and its complications, comprising administrating a probiotic composition, wherein the probiotic composition comprises supernatant of the live bacterial cultures of *Lactobacillus reuteri* GMNL-89 with the deposition number of CCTCC M 207154; wherein the live bacterial cultures are cultured at least 16 hours; wherein the supernatant is filtrated via filter membrane to filter out bacteria cells; the total protein of the administrating supernatant is adjusted to 20 μg/ml or 100 μg/ml; a daily dose of the administrating supernatant is 9.7 mL/day.

2. The method of claim 1, wherein the probiotic composition is a pharmaceutical composition, food or their combinations thereof.

3. The method of claim 2, wherein the pharmaceutical composition further comprises a pharmaceutically acceptable vehicle.

4. The method of claim 2, wherein the pharmaceutical composition is in a dosage form suitable for oral administration.

5. The method of claim 4, wherein the dosage form is selected from the group consisting of solutions, suspensions, emulsions, powders, tablets, pills, syrups, lozenges, troches, chewing gums, slurries and capsules.

6. The method of claim 2, wherein the food further comprises at least one probiotic bacteria strain selected from the group consisting of *Lactobacillus* sp., *Bifidobacterium* sp., *Streptococcus* sp. and yeasts.

7. The method of claim 2, wherein the food further comprises an edible material, the edible material comprises water, fluid milk products, milk, concentrated milk, fermented milk, yogurt, sour milk, frozen yogurt, lactic acid bacteria-fermented beverages, milk powder, ice cream, cream cheese, dry cheese, soybean milk, fermented soybean milk, vegetable-fruit juices, juices, sports drinks, confectioneries, jellies, candies, infant formulas, health foods, animal feeds, Chinese herbs or dietary supplements.

8. The method of claim 1, wherein the complications of type 2 diabetes is selected from the group consisting of diabetic neuropathy, renal diseases, inflammation, cardiovascular complications, high cholesterol complications, eye diseases, and liver diseases.

9. A method of inhibiting high blood glucose levels, high glycosylated hemoglobin ratios, high total cholesterol levels, high liver triglyceride concentrations, high low density lipoprotein (LDL), high homeostasis model assessment (HOMA) indicator, high tumor necrosis factor a (TNF-α), high Interleukin-1 R (IL-10) or high interleukin-6 (IL-6), comprising administrating a probiotic composition, wherein the probiotic composition comprises supernatant of live bacterial culture of *Lactobacillus reuteri* GMNL-89 with a deposition number of CCTCC M 207154; wherein the live bacterial cultures are cultured at least 16 hours: wherein the supernatant is filtrated via filter membrane to filter out bacteria cells: the total protein of the administrating supernatant is adjusted to 20 µg/ml or 100 µg/ml: a daily dose of the administrating supernatant is 9.7 mL/day.

10. A method of increasing high density lipoprotein (HDL), the activity of superoxide dismutase (SOD) or the activity of glutathione peroxidase (GSH-Px), comprising administrating a probiotic composition, wherein the probiotic composition comprises supernatant of live bacterial culture of *Lactobacillus reuteri* GMNL-89 with a deposition number of CCTCC M 207154; wherein the live bacterial cultures are cultured at least 16 hours: wherein the supernatant is filtrated via filter membrane to filter out bacteria cells: the total protein of the administrating supernatant is adjusted to 20 µg/ml or 100 µg/ml: a daily dose of the administrating supernatant is 9.7 mL/day.

* * * * *